United States Patent [19]

McDonnell Bushnell et al.

[11] Patent Number: 5,290,586
[45] Date of Patent: Mar. 1, 1994

[54] METHOD TO MONITOR META-PAETE CURE ON METALLIZED SUBSTRATES

[75] Inventors: Lorraine P. McDonnell Bushnell, Carmel; Judith A. Coffin, Pleasant Valley; Guillermo Prada-Silva, Wappingers Falls, all of N.Y.

[73] Assignee: International Business Machines Corporation, Armonk, N.Y.

[21] Appl. No.: 942,861

[22] Filed: Sep. 10, 1992

[51] Int. Cl.$^5$ ............................................. B05D 1/00
[52] U.S. Cl. ....................................... 427/8; 427/521; 427/557; 427/9
[58] Field of Search ................... 427/8, 521, 557, 9; 356/355, 357, 361

[56] References Cited

U.S. PATENT DOCUMENTS

| | | |
|---|---|---|
| 3,150,264 | 9/1964 | Ehlert . |
| 3,524,983 | 8/1970 | Voelz ................................. 356/51 |
| 3,930,730 | 1/1976 | Laurens .............................. 356/357 |
| 4,254,337 | 3/1981 | Yasujima ............................ 356/375 |
| 4,496,697 | 1/1985 | Zsolnay et al. . |
| 4,633,087 | 12/1986 | Rosenthal et al. . |
| 4,643,910 | 2/1987 | Foutz ................................. 427/8 |
| 4,777,431 | 10/1988 | Day et al. . |
| 4,874,948 | 10/1989 | Cielo et al. . |
| 4,891,591 | 1/1990 | Johnston et al. . |
| 4,984,894 | 1/1991 | Kondo ............................... 356/357 |

FOREIGN PATENT DOCUMENTS

| | | |
|---|---|---|
| 9091093 | 5/1984 | Japan ............................. 427/557 |
| 224607 | 9/1989 | Japan ............................. 356/355 |

OTHER PUBLICATIONS

R. D. Pierce et al "Thickness Measurements of Films on Transparent Substrates by Photoelectric Detection of Interference Fringes" Rev. Sci. Instrum. vol. 45, No. 1, Jan. 1974, pp. 14–15.

R. Ginsburg et al "Cure Monitor for Process Control" IBM Technical Disclosure Bulletin vol. 25, No. 8, Jan. 1983, p. 4355.

S. Guruswamy et al. "Radiation Curing of Organic Coatings" Metal Finishing, Jul. 1978, pp. 25–30.

*Primary Examiner*—Shrive Beck
*Assistant Examiner*—Vi Duong Dang
*Attorney, Agent, or Firm*—Whitham & Marhoefer

[57] ABSTRACT

Microreflectance infrared (IR) spectroscopy is used to determine the degree of cure of Meta-Paete (pyromellitic dianhydride-oxydianiline ethyl ester) films on metallized substrates. In this method, the infrared bands at 1028 and 1015 cm$^{-1}$ are used to indirectly monitor ethanol evolution during Meta-Paete cure. The 1015 cm$^{-1}$ band serves as internal reference, while the 1028 cm$^{-1}$ band, which corresponds to the C—O stretch in the ethoxy group, is used to monitor imidization through loss of the ethoxy group during cure. Quantification of ethanol evolution is possible, since no apparent distortion is observed in the external reflection spectra at these two frequencies. The method can also be applied to measure the cure uniformity of Meta-Paete films, to provide an estimate of film thickness over metallized substrates, and to monitor temperature uniformity in an oven cavity.

8 Claims, 4 Drawing Sheets

METHOD TO MONITOR META-PAETE CURE ON METALLIZED SUBSTRATES

BACKGROUND OF THE INVENTION

1. Field of the Invention

The invention is generally related to electronic component manufacturing, including printed circuit board (PCB) and integrated circuit (IC) manufacturing. More particularly, this invention is related to an in-line monitor for non-destructively evaluating the state of cure and percent imidization of thick (>1 μm) meta-paete (pyromellitic dianhydride-oxydianiline ethyl ester) polyimide films.

2. Description of the Prior Art

Ginsburg et al., IBM Technical Disclosure Bulletin Vol. 25, No. 8, January 1983, discloses that Fourier transform infrared (FTIR) spectroscopy techniques have been used in the past to monitor the degree of imidization of polyimide work pieces. The detected degree of imidization can be used to adjust on-line fabrication parameters.

U.S. Pat. No. 3,524,983 to Voeltz discloses a process and apparatus for determining the cure characteristics of materials which utilizes infrared radiation that is passed through a sample and reflected back through the sample by a reflective surface which supports the sample. A sensor monitors changes in the intensity of the reflected beam and the cure characteristics are determined by absorption changes.

SUMMARY OF THE INVENTION

It is an object of this invention to provide a method for determining the degree of cure or percent imidization of meta-paete polyimide films which is based on microreflectance of infrared energy that is easily adaptable to PCB and IC manufacturing environment.

It is another object of this invention to provide a method for monitoring the degree of cure or percent imidization of meta-paete polyimide films which uses the ratio of the intensity of reflected 1028 $cm^{-1}$ and 1015 $cm^{-1}$ bands.

It is still another object of this invention to provide a method of determining the cure uniformity of a meta-paete polyimide film using the ratio of the intensity of reflected 1028 $cm^{-1}$ and 1015 $cm^{-1}$ bands.

It is still another object of this invention to provide a method of determining the temperature conditions within an oven cavity by monitoring the degree of cure of meta-paete polyimide films coated on parts that are positioned at different locations within the oven.

It is yet another object of this invention to provide a method for non destructively determining the thickness of meta-paete films which utilizes the fringing effects of reflected near infrared radiation from the surface of a meta-paete film and from a reflective surface under the meta-paete film.

According to the invention, a meta-paete polyimide film is monitored using infrared radiation that is reflected from a metallized surface underneath the meta-paete film. It has been discovered that the 1028 $cm^{-1}$ and 1015 $cm^{-1}$ bands are distortion free and that a ratio of the intensities of the 1028 $cm^{-1}$ and 1015 $cm^{-1}$ bands can be used to discern the degree of cure or percent imidization of the meta-paete film. Meta-paete films having a range of 1028/1015 ratios between 0.3 and 0.6 have been found to have a desirable intermediate state of cure. The intermediate state of cure allows successive layers of meta-paete film to be applied without cracking or crazing of the lower layer, as would occur when the lower layer is undercured and interacts with the solvent for the succeeding layer. The intermediate state of cure allows successive layers of meta-paete film to be applied without delamination, as would occur when the underlying meta-paete film is overcured and prohibits interfacial diffusion. By monitoring the 1028 $cm^{-1}$ and 1015 $cm^{-1}$ bands at different locations on a meta-paete polyimide coating, the uniformity of the cure can be assessed. For example, the 1028/1015 ratio can be used to determine the degree of cure of the meta-paete polyimide coating at different locations and the uniformity of the cure can be assessed from the extent of correlation between degree of cure at the different locations. In addition, by monitoring the degree of cure of meta-paete polyimide coatings using the 1028/1015 ratio for coatings which are positioned at different locations within an oven cavity, the uniformity of curing within the oven cavity can be assessed. Furthermore, the interference fringes in the near infrared that result from combining radiation reflected from a meta-paete film surface and radiation reflected from a metallic surface underneath the meta-paete film can be used to estimate the thickness of the meta-paete film.

BRIEF DESCRIPTION OF THE DRAWINGS

The foregoing and other objects, aspects and advantages will be better understood from the following detailed description of the preferred embodiments of the invention with reference to the drawings, in which.

DETAILED DESCRIPTION OF THE PREFERRED EMBODIMENTS OF THE INVENTION

Figure 1:
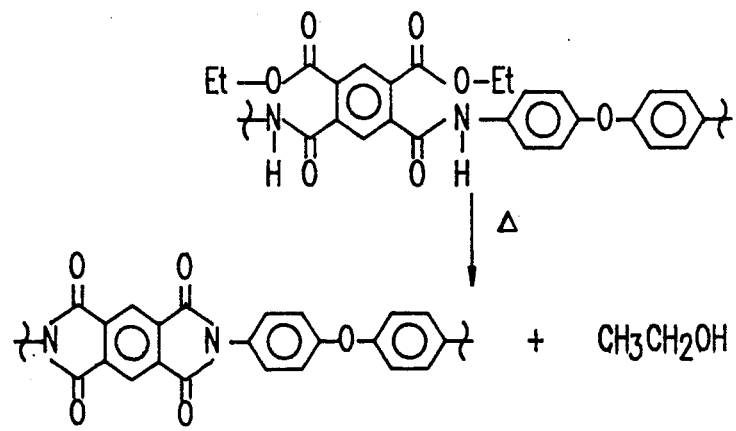
FIG. 1 is a schematic diagram showing the thermal imidization of meta-paete.

FIG. 1 shows that meta-paete polyimide films are formed by a thermal imidization reaction which results in an imidized polymer and the evolution of ethanol. While FIG. 1 shows pyromellitic dianhydride-4,4'-oxydianiline (PMDA-ODA) resulting from the thermal imidization reaction, other conventional polymers, such as 3,3', 4,4'-biphenyltetracarboxylic acid dianhydride-4,4'-oxydianiline (BPDA-ODA), BTDA ODA, 6FDA-ODA, and the like, are formed by similar thermal imidization processes. Meta-paete polyimide films are used by PCB and IC manufacturers as stress-relief layers in multilayer glass ceramic packages, semiconductor chips, etc., and as dielectric materials for device isolation.

Figure 2:
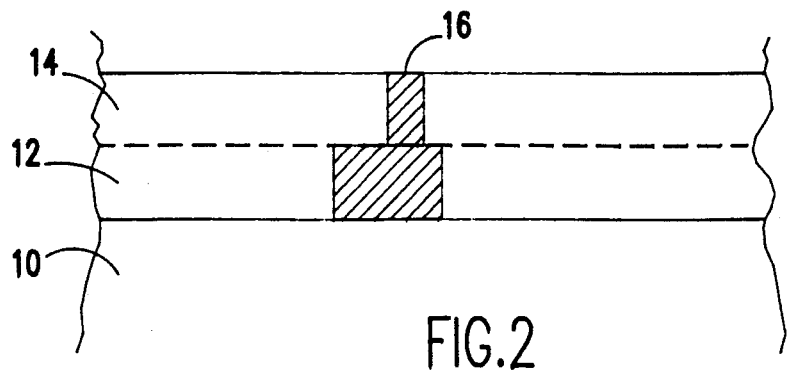
FIG. 2 is a cross-sectional side-view of a structure with two layers of meta-paete applied thereon.

FIG. 2 shows that thick coatings (>1 $\mu$m) of meta-paete are typically applied to substrates 10 (e.g., silicon, glass, glass-ceramic, etc.) as two or more layers 12 and 14. Each of the layers 12 and 14 can accommodate metallization 16 in the form of pads, vias, conducting lines, etc., of different sizes and shapes. The layers 12 and 14 are typically applied by spin-coating, although other processes, such as spraying, dip coating, etc., can also be used. Prior to applying the top layer 14 onto layer 12, layer 12 must be partially cured. The intermediate degree of cure of the first meta-paete layer 12 is extremely important to product functionality. A very high degree of cure will lead to poor interlayer diffusion and delamination from the second layer 14, whereas a low degree of cure will result in swelling and cracking/-crazing of the first layer 12 when exposed to the solvent, typically n methyl pyrolidone (NMP) or an aprotic solvent such as dimethyl formamide (DMF), from the second layer 14.

Fourier transform infrared (FTIR) spectroscopy has been used to study the cure kinetics of polyimides. In most cases, infrared measurements have been made by transmission through thin, free-standing films that are on the order of 1 $\mu$m or less in thickness, or through thin films cast onto infrared transparent discs. The thermal imidization of meta-paete can be readily followed by transmission infrared spectroscopy on free-standing films. Depending on the thickness of the film, any of the characteristic imide ring bands at 1780 cm$^{-1}$ (symmetric C=O stretch), 1380 cm$^{-1}$ (C—N stretch), or 725 cm$^{-1}$ (C=O bending) can be used to monitor the kinetics of the reaction.

The 1015 cm$^{-1}$ band corresponds to the out-of-plane C—C—H bending in the aromatic rings from oxydianiline, and can serve as an internal reference. As will be discussed in more detail below, working with 7-11 $\mu$m thick meta-paete films, it was determined that internally consistent measurements of imide content could be obtained through the entire cure range by using the 725 cm$^{-1}$ band from a transmission spectra, in conjunction with the 1015 cm$^{-1}$ band as an internal standard.

The degree of cure of meta-paete can also be determined by using thermogravimetric analysis in combination with mass spectrometry (TGA-MS). In this process, TGA-MS is used to monitor the relative amount of ethanol evolved during imidization. Integration of the total ion chromatogram as a function of temperature allows calculation of the percent of total alcohol evolved and, thus, percent imidization can be determined.

This invention is particularly concerned with a microreflectance infrared method which allows for the determination of the degree of cure of meta-paete films on metallized substrates. Traditionally, infrared reflectance measurements have not been used for determining the degree of cure of thick (>1 $\mu$m) polymer films. This is due to the fact that variations in index of refraction and extinction coefficient as a function of wavelength usually result in considerable band distortions in the reflectance spectra. However, it has been discovered that microreflectance infrared methods can be used with certain bands (1028 cm$^{-1}$ and 1015 cm$^{-1}$) that have low extinction coefficients to monitor the degree of meta-paete cure.

A series of experiments were conducted where infrared spectra were acquired using an IR PLAN microscope, available from Spectra Tech, Inc., equipped with an MCT detector and attached to a Nicolet 740 system spectrometer. Reflectance attachments were taken at near normal incidence using a 100 $\mu$m sampling area. All of the spectra acquired represent 256 scans collected at 4 cm$^{-1}$ resolution using triangular apodization.

Figure 3:
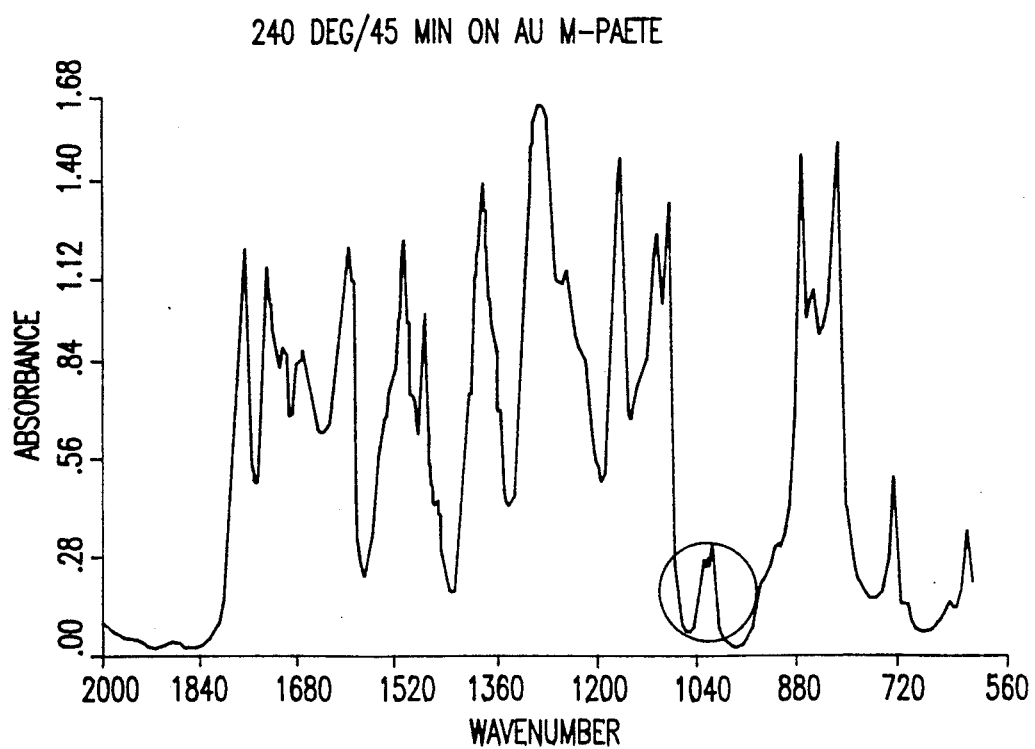
FIG. 3 is a graph showing the infrared microreflectance spectra of a meta-paete film.

FIG. 3 shows the microreflectance spectra of an 8 $\mu$m thick meta-paete film which had been partially cured by heating at 240° C. for 45 minutes. The measurement was made on a glass ceramic substrate by reflecting the micro IR beam (100 $\mu$m beam diameter at the sample plane) off gold pads positioned on the substrate surface under the film. The microreflectance spectra may also be referred to as a reflection-absorption spectra. FIG. 3 shows that severe distortion occurs in the shape of the high intensity bands. However, the bands at 1015 and 1028 cm$^{-1}$ appear to be distortion free.

Figure 4:
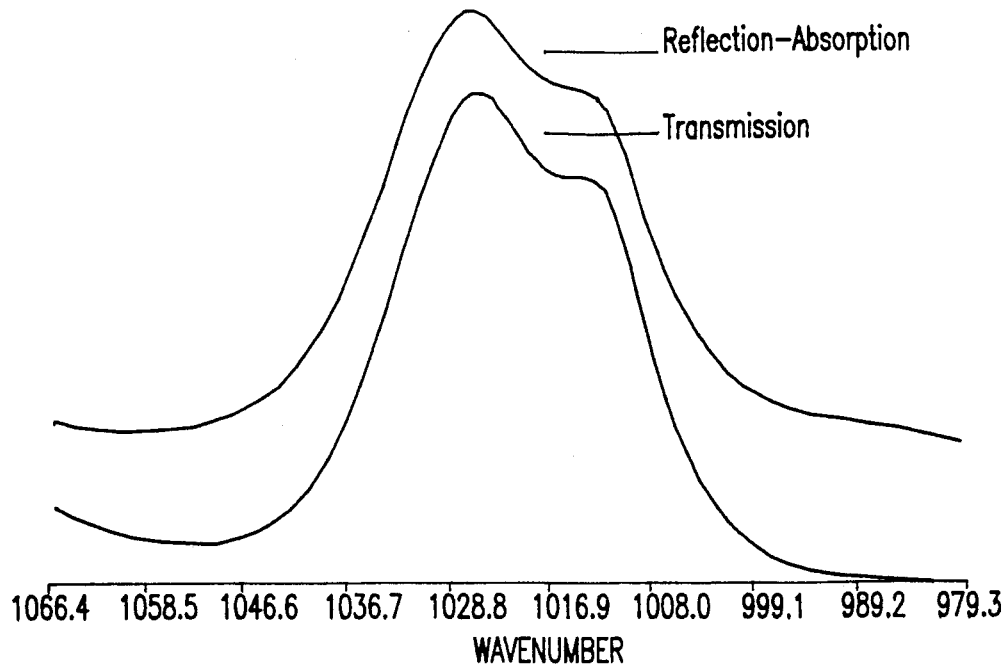
FIG. 4 is a graph showing a comparison of an infrared spectra made by transmission through a meta-paete film and an infrared spectra made by microreflectance.

FIG. 4 shows two infrared spectra obtained on a 11 $\mu$m thick meta-paete film which had been cured at 210° C. for 45 minutes. The reflection-absorption spectra was obtained by reflecting the IR beam off an underlying gold pad as described above. Other reflective surfaces besides gold, e.g., aluminum, copper, Al-Cu alloys, etc., that are commonly used in PCB and IC manufacture can be used when determining reflection-absorption spectra of a meta-paete film in an in-line processing environment. The transmission spectra was obtained by passing the IR beam directly through the film and sensing the absorption of the transmitted beam. As can be seen from FIG. 4, the reflection-absorption spectra and transmission spectra have the same relative intensities of the 1028 cm$^{-1}$ and 1015 cm$^{-1}$ bands.

Using this discovery, experiments were conducted to determine if the ratio of the intensities of the 1028 cm$^{-1}$ and 1015 cm$^{-1}$ bands were approximately the same throughout the imidization range when determined by IR transmission or IR reflection-absorption. Table 1 presents the ratio of the relative intensity of the 1028 cm$^{-1}$ band to the 1015 cm$^{-1}$ band for meta-paete films ranging between 7 $\mu$m and 11 $\mu$m thick which have been heated for 45 minutes at varying temperatures from IR spectra obtained by transmission through the film and by reflection-absorption (microreflectance).

TABLE 1

| Temperature °C. | Ratio of Relative Intensity for IR Absorption at the 1028 cm$^{-1}$ and 1015 cm$^{-1}$ Bands by Transmission and Reflection-Absorption | |
|---|---|---|
| | 1028/1015 | |
| | Trans. | Ref.-Abs. |
| 210 | 1.18 | 1.22 |
| 230 | 0.88 | 0.84 |
| 245 | 0.64 | 0.62 |
| 300 | 0.17 | 0.20 |

As can be seen from Table 1, the 1028/1015 ratio is approximately the same when partially cured meta-paete films are analyzed using IR transmission techniques and using IR reflection-absorption techniques. These data confirm that both the 1028 cm$^{-1}$ and 1015 cm$^{-1}$ bands are distortion-free when obtained in the microreflectance mode; therefore, as will be explained below, microreflectance IR measurements of the 1028 cm$^{-1}$ and 1015 cm$^{-1}$ bands can be used to monitor the degree of cure of meta-paete films. Reflection absorption (microreflectance) measurements are much more amenable to the PCB and IC manufacturing environment than transmission measurements since the meta-paete films on the substrates being manufactured can be monitored from above the substrate using the capture pads and metallized lines on the substrate as a reflective surface.

Figure 5:
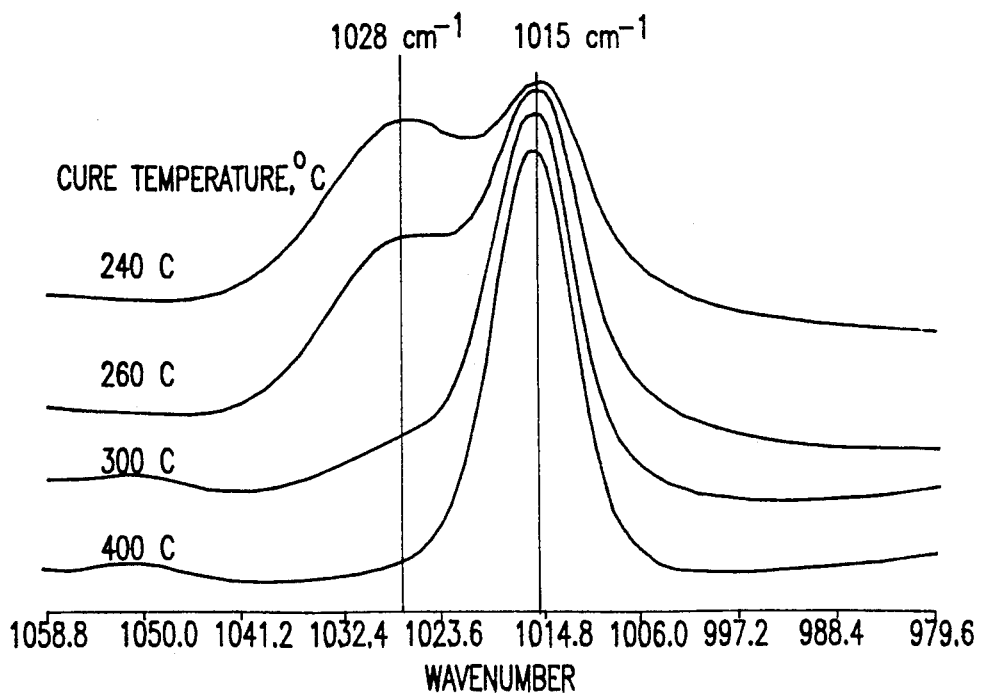
FIG. 5 is a graph showing the variation of meta-paete IR bands at 1015 $cm^{-1}$ and 1028 $cm^{-1}$ as a function of varying cure temperatures.

From the data in Table 1, it can be seen that the 1028/1015 ratio can be used to monitor the cure of meta-paete films. As pointed out above, the 1015 cm$^{-1}$ band corresponds to the out-of-plane C—C—H bending in the aromatic rings from oxydianiline and serves as an internal reference. The 1028 cm$^{-1}$ band is assigned to the C—O stretch in the ethoxy group. As the ethoxy group is eliminated from the meta-paete film through imidization and evolution of ethanol, the 1028/1015 ratio should decrease. The data shown in Table 1 confirm the decrease in 1028/1015 ratio, wherein films cured at higher temperatures that would have a greater degree of cure and percent imidization did have lower 1028/1015 ratios. Furthermore, FIG. 5 graphically shows that as 7-11 μm thick meta-paete films are cured at 240° C., 260° C., 300° C., and 400° C. for 45 to 55 minutes, the intensity of the 1028 cm$^{-1}$ drops considerably, indicating that less ethanol is present in the more fully cured films.

Figure 6:
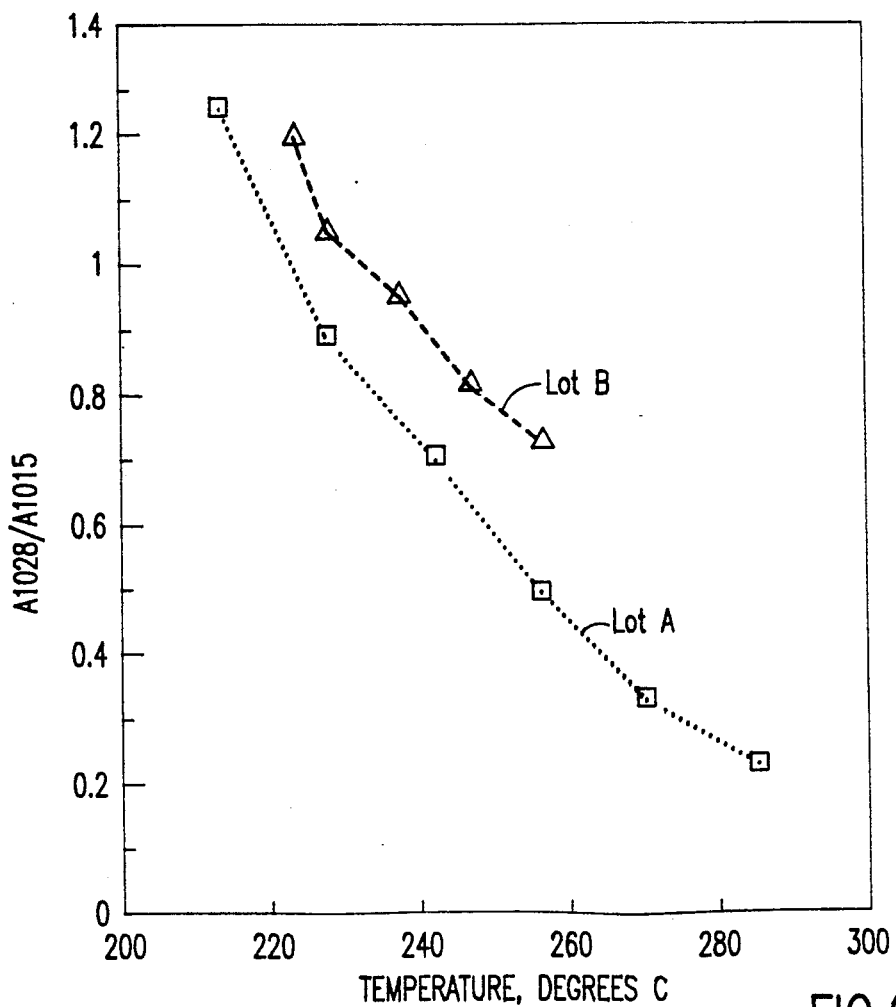
FIG. 6 is a graph showing the ratio of reflection-absorption IR intensities at 1028 $cm^{-1}$ to 1015 $cm^{-1}$ at different cure temperatures for two different meta-paete lots.

FIG. 6 shows a plot of A1028/A1015 as a function of cure temperature for films from two meta-paete lots. The datapoints on the graph were generated by curing the 7-11 μm thick meta-paete films at the respective temperatures for 50 minutes. Lot A cured at a much faster rate than Lot B as can be seen, for example, by observing that the meta-paete film of Lot A had a 1028/1015 value of 0.50 after a cure at 255° C. for 50 minutes while the meta-paete film of Lot B had a 1028/1015 value of 0.73. The difference between lots could be a function of handling or other factors which influence the chemistry of the meta-paete films.

The meta-paete films of Lot A and Lot B which were exposed to an intermediate cure of 255° C. for 50 minutes were subsequently overcoated with a second meta-paete layer. The Lot A meta-paete films which had a 1028/1015 ratio of 0.50 processed without any problems; however, the Lot B meta-paete films which had a lower degree of cure and a 1028/1015 ratio of 0.73 exhibited cracking and crazing as a result of exposure to the NMP solvent from the second meta-paete layer. In general, partially cured meta-paete films with 1028/1015 ratios ranging from 0.30 to 0.60 exhibited no cracking or crazing, or delamination between the two meta-paete coats. Hence, in an in-line processing environment, microreflectance IR can be used to determine the 1028/1015 ratio of curing meta-paete films. Overcoating the meta-paete films with a second layer will preferably proceed when the 1028/1015 ratio for the first layer is between 0.3 and 0.6 in order to avoid cracking and crazing problems as well as delamination problems.

Chemically, the 1028/1015 ratio corresponds to the relative amount of ethanol evolved during cure, where smaller 1028/1015 ratios indicate a higher degree of cure because less of the ethoxy group is present in the meta-paete film, and, thus, the 1028/1015 ratio can also be related to relative imidization. In experiments with a series of 7-11 μm thick meta-paete films, the percent imidization was calculated from a ratio of the 725 cm$^{-1}$ imide absorbance and the 1015 cm$^{-1}$ C—C—H oxydianiline bend (internal standard) from IR transmission spectra. IR transmission spectra were made on a free standing film that was cured on a silicon wafer and subsequently removed. The absorbances at 725 and 1015 cm$^{-1}$ were chosen because they obey Beer's Law for 7-11 μm meta-paete films. All relative imidization values are based on a ratio of 3.20 which is arbitrarily defined as 100%. This eliminates variations in the 725/1015 ratio corresponding to 100% imidization which would probably be due to chain orientation effects observed at various annealing conditions.

Figure 7:
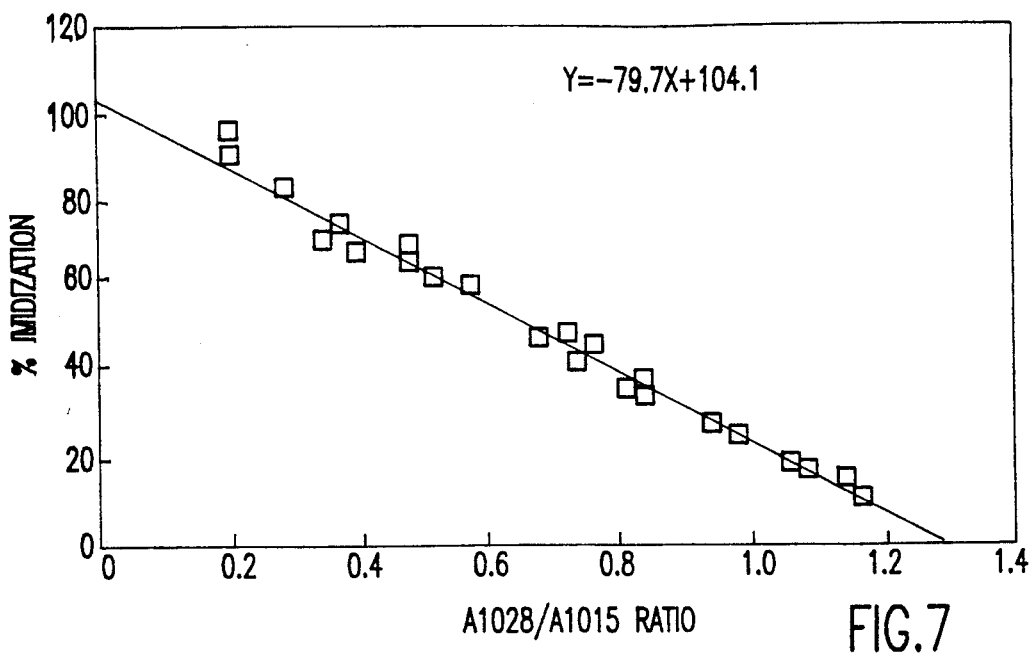
FIG. 7 is a graph which relates the ratio of transmission IR intensities at 725 $cm^{-1}$ and 1015 $cm^{-1}$ to the ratio of intensities at 1028 $cm^{-1}$ and 1015 $cm^{-1}$.

FIG. 7 plots the correlation between percent imidization of the 7-11 μm thick meta-paete films cured at any given temperature, expressed by ([725/1015]/3.20), and the 1028/1015 ratio. FIG. 7 shows that there is an inverse linear relationship in the percent imidization determined by 725/1015 ratios and the 1028/1015 ratio. This is because higher relative imidization, as measured by increased 725 cm$^{-1}$ absorbance, corresponds to a smaller relative amount of ethoxy groups, as measured by decreased 1028 cm$^{-1}$ absorbance, remaining in the polyamic ethyl ester precursor. The line in FIG. 7 can be described by the following mathematical relationship: $Y = -79X + 104.1$, where Y is the percent imidization and X is the ratio of absorbances at 1028 cm$^{-1}$ and 1015 cm$^{-1}$.

As shown previously in connection with FIG. 4 and Table 1, the same A1028/A1015 ratio is obtained in transmission and reflection-absorption spectra. Therefore, absorbance ratios from microreflectance measurements can be used to readily calculate the percent imidization of meta-paete films on metallized substrates. By employing this method, manufacturing processability has been confirmed for partially cured meta-paete films with 1028/1015 ratios between 0.30 and 0.60, which correspond to relative imidization values ranging from 55% to 80%. However, cracking and crazing of a first layer meta-paete film was found for films with 1028/1015 absorbance ratios greater than 0.73, or imidization values less than 45%.

By reflecting a micro infrared beam off capture pads on a substrate located at the center of the substrate and at its edges, the cure uniformity of a first meta-paete layer on a substrate can be measured. Table II presents data for two substrates on which 11 μm thick meta-paete films which had been partially cured at 255° C. for 55 minutes.

TABLE II

| Non-Destructive Determination of Degree of Cure on Meta-Paete Coated Substrates by FTIR | | |
|---|---|---|
| SUBSTRATE # | 1028/1015 | |
| | Corners | Center |
| 1 | 0.73 ± 0.02 | 0.73 |
| 2 | 0.75 ± 0.02 | 0.72 |

As indicated from the 1028/1015 ratios, Table II shows that both substrates have the same degree of cure and that the meta-paete film cured uniformly in both the center of the substrate and at the corners. As pointed out above, the 1028/1015 ratios of 0.73 indicate an imidization of approximately 45%, hence, for processing purposes, both substrates are undercured and should be heated at higher temperatures or for longer periods of time to cure the meta-paete films to a point where they will not be cracked or crazed by the NMP solvent during application of a second meta-paete coat.

It is expected that monitoring the 1028 cm$^{-1}$ and 1015 cm$^{-1}$ bands at different locations on a meta-paete polyimide coating, as was done for the two substrates described above in conjunction with Table II, can be a valuable procedure for assessing the uniformity of cure of meta-paete polyimide coatings on substrates being processed in a manufacturing line. If the edges of meta-paete polyimide coatings on substrates are curing faster than other regions, then adjustments could be made to the manufacturing procedures. For example, the 1028/1015 ratio can be used to determine the degree of cure of the meta-paete polyimide coating at different locations on a substrate and the uniformity of the cure can be assessed from the extent of correlation between degree of cure at the different locations. Furthermore, it is expected that monitoring the 1028 cm$^{-1}$ and 1015 cm$^{-1}$ bands on meta-paete polyimide coatings on substrates that are positioned at different locations within an oven cavity can provide insight into the temperature uniformity within the oven cavity. For example, if the degree of cure for meta-paete polyimide coatings, as determined from the 1028/1015 ratio, on substrates positioned at different locations within the oven cavity are not approximately the same, the temperature conditions within the oven are not uniform (i.e., hotter conditions in one area of the oven cavity result in a greater degree of cure for the meta-paete films on substrates located in that area). Temperature uniformity is a particular problem with microwave ovens.

Figure 8:
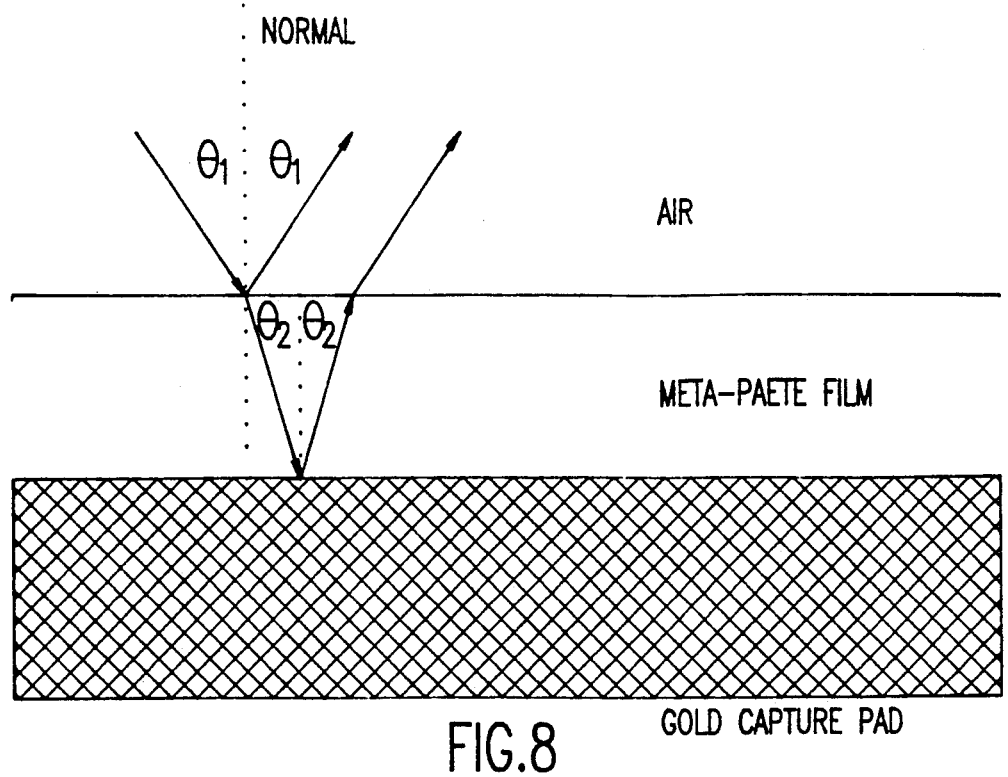
FIG. 8 is a cross-sectional side view of a capture pad overcoated with a meta-paete film which shows an angle of incidence to the meta-paete film and an angle of refraction.
Figure 9:
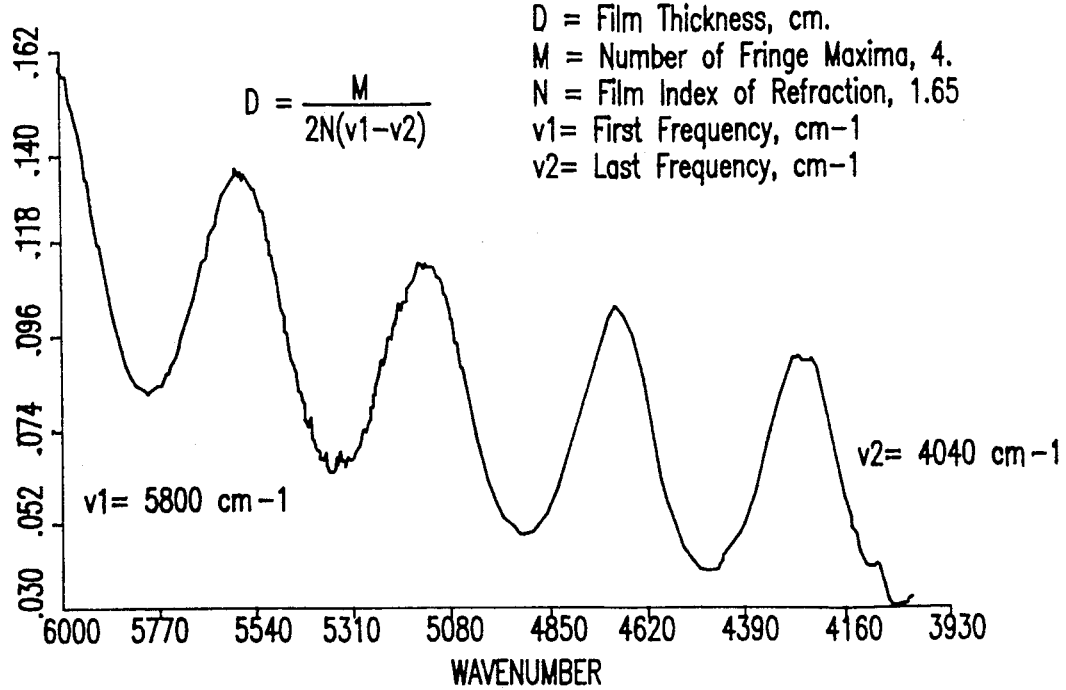
FIG. 9 is a near infrared spectra showing interference fringes used for determining the thickness of meta-paete films.

FIGS. 8 and 9 demonstrate that interference fringes in the near-infrared region which result when using the microreflectance technique can be used to provide a measurement of meta-paete film thickness. FIG. 8 shows that interference fringes result when meta-paete reflected IR beam is recombined with the IR beam reflected from the gold or other reflective surface underlying the meta-paete film. As shown in FIG. 8, the angle of incidence, $\theta_1$, at the air/meta-paete surface results in a mirror image reflection; however, light which is refracted by the meta-paete film has an angle of refraction, $\theta_2$, that offsets the light reflected by the gold pad. Assuming that no phase shift occurs at the meta-paete gold interface and that the reflectivity variation at the air/meta-paete and meta-paete/gold interfaces is negligible, meta-paete film thickness can be expressed by Equation 1:

$$D = M/(2(N^2 - SIN^2\theta)^{0.5}(V_1 - V_2)) \qquad \text{Eq. 1}$$

where D is the film thickness in centimeters, M is the number of fringe maxima, N is the film refractive index, $\theta$ is the IR beam angle on incidence, $V_1$ is the first frequency in cm$^{-1}$, and $V_2$ is the last frequency in cm$^{-1}$. In the present case, the IR beam had a normal incidence to the sample surface. Therefore, the film thickness can be calculated from a simplified Equation 2.

$$D = M/2N(V_1 - V_2) \qquad \text{Eq. 2}$$

where it is assumed that the refractive index is constant over the frequency range from $V_1$ to $V_2$.

FIG. 9 shows fringes in the near infrared region for one particular meta-paete film obtained using the microreflectance technique. The meta-paete film thickness can be determined to be 6.9 $\mu$m based on the number of fringe maxima being 4, the film index of refraction being 1.65, $V_1$ being 5800 cm$^{-1}$, and $V_2$ being 4040 cm$^{-1}$.

While the invention has been described in terms of its preferred embodiments, those skilled in the art will realize that the invention can be practiced with modification within the spirit and scope of the appended claims.

Having thus described our invention, what we claim as new and desire to secure by Letters Patent is as follows:

1. A method to non-destructively monitor the cure of meta-paete films, comprising the steps of:
   exposing a substrate having a meta-paete polyimide film that is one micron or greater in thickness to infrared radiation;
   monitoring the 1015 cm$^{-1}$ and 1028 cm$^{-1}$ bands reflected from a reflective surface positioned under said meta-paete polyimide film; and
   determining a degree of cure or percent imidization of said meta-paete polyimide film from a ratio of the intensity of said 1028 cm$^{-1}$ band to said 1015 cm$^{-1}$ band.

2. A manufacturing process, comprising the steps of:
   applying a coating of meta-paete polyimide film to a surface of a substrate, said surface of said substrate having a reflecting material thereon;
   partially curing said coating of meta-paete polyimide film;
   exposing said coating of meta-paete polyimide film to infrared radiation;
   monitoring the 1015 cm$^{-1}$ and 1028 cm$^{-1}$ bands reflected from said reflective surface positioned on said substrate under said meta-paete polyimide film; and
   calculating a ratio of the intensity of said 1028 cm$^{-1}$ band to said 1015 cm$^{-1}$ band.

3. A manufacturing process as recited in claim 2 further comprising the step of applying a second coating of meta-paete polyimide film to said coating of meta-paete polyimide film when said ratio of the intensity of said 1028 cm$^{-1}$ band to said 1015 cm$^{-1}$ band ranges from 0.3 to 0.6.

4. A manufacturing process as recited in claim 2 further comprising the step of determining a degree of cure of said coating of meta-paete polyimide film from said ratio of the intensity of said 1028 cm$^{-1}$ band to said 1015 cm$^{-1}$ band calculated in said calculating step.

5. A manufacturing process as recited in claim 2 further comprising the step of determining a percentage of imidization of said coating of meta-paete polyimide film from said ratio of the intensity of said 1028 cm$^{-1}$ band to said 1015 cm$^{-1}$ band calculated in said calculating step.

6. A manufacturing process as recited in claim 5 further comprising the step of applying a second coating of meta-paete polyimide film to said coating of meta-paete polyimide film when said percentage of imidization ranges from 55 to 80 percent.

7. A manufacturing process as recited in claim 2 further comprising the step of assessing a cure uniformity for said meta-paete polyimide film by comparing a first calculated ratio of the intensity of said 1028 cm$^{-1}$ band to said 1015 cm$^{-1}$ band for reflected radiation from a first portion of said substrate to a second calculated ratio of the intensity of said 1028 cm$^{-1}$ band to said 1015 cm$^{-1}$ band for reflected radiation from a second portion of said substrate.

8. A method for monitoring temperature uniformity in an oven cavity, comprising the steps of:

applying coatings of meta-paete polyimide film to surfaces of a plurality of substrates, said surfaces of said substrates each having a reflecting material thereon;

positioning said substrates at different locations inside an oven cavity;

partially curing said coatings of meta-paete polyimide film;

exposing said coatings of meta-paete polyimide film to infrared radiation;

monitoring the 1015 cm$^{-1}$ and 1028 cm$^{-1}$ bands reflected from said reflective surfaces positioned on said substrates under said coatings of meta-paete polyimide film;

calculating a ratio of the intensity of said 1028 cm$^{-1}$ band to said 1015 cm$^{-1}$ band for each of said substrates;

determining if each ratio calculated in said calculating step is approximately equal, whereby approximately equal ratios indicate temperature uniformity within said oven cavity and unequal ratios indicate a lack of temperature uniformity within said oven cavity.

* * * * *